(12) United States Patent
Shuaib et al.

(10) Patent No.: US 8,479,589 B2
(45) Date of Patent: *Jul. 9, 2013

(54) METHOD AND APPARATUS FOR CHARACTERIZING MICROSCALE FORMABILITY OF THIN SHEET MATERIALS

(75) Inventors: Nasr A. Shuaib, Lexington, KY (US); Marwan K. Khraisheh, Lexington, KY (US)

(73) Assignee: University of Kentucky Research Foundation, Lexington, KY (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/229,117

(22) Filed: Sep. 9, 2011

(65) Prior Publication Data
US 2011/0314906 A1    Dec. 29, 2011

Related U.S. Application Data

(63) Continuation of application No. 12/177,968, filed on Jul. 23, 2008, now Pat. No. 8,042,405.

(51) Int. Cl.
*G01N 19/08* (2006.01)
(52) U.S. Cl.
USPC ................................ 73/799; 73/760
(58) Field of Classification Search
USPC .................................... 73/760, 799
See application file for complete search history.

(56) References Cited

U.S. PATENT DOCUMENTS

| | | | | |
|---|---|---|---|---|
| 5,569,342 | A  * | 10/1996 | Gould et al. | 156/64 |
| 6,688,201 | B1 * | 2/2004 | Dokyu et al. | 83/206 |
| 2006/0008707 | A1 * | 1/2006 | Watanabe et al. | 430/5 |

* cited by examiner

*Primary Examiner* — Lisa Caputo
*Assistant Examiner* — Octavia Hollington
(74) *Attorney, Agent, or Firm* — King & Schickli, PLLC (57) ABSTRACT

A method of predicting sheet formability at a microscale level includes the steps of providing a grid pattern on a test sheet, bulging the test sheet to a hemispherical shape until a crack is initiated on the surface of the test sheet, detecting the initiation of the crack, acquiring two images of the surface adjacent to the crack and calculating surface strains on the test sheet.

20 Claims, 9 Drawing Sheets

METHOD AND APPARATUS FOR CHARACTERIZING MICROSCALE FORMABILITY OF THIN SHEET MATERIALS

This application is a continuation of prior U.S. patent application Ser. No. 12/177,968 filed on 23 Jul. 2008 now U.S. Pat. No. 8,042,405 and entitled "Method and Apparatus for Characterizing Microscale Formability of Thin Sheet Materials", the entire disclosure of which is incorporated herein by reference.

TECHNICAL FIELD AND INDUSTRIAL APPLICABILITY OF THE INVENTION

The present invention relates generally to a method and apparatus for studying the formability of sheet materials at different strain conditions and more specifically to the formability of sheet metals for microscale applications.

BACKGROUND OF THE INVENTION

The increasing demand for microparts and products has prompted the industry to focus on more efficient ways to better supply such consumables. This continuous demand is pushed by consumers as well as industries that are relying more on smaller products with diverse applications. Metal forming processes are well known for displaying high productivity and better material utilization. Applying these forming technologies on the microscale level is significant for achieving parts with intricate geometries and configurations, which is an essential issue in such a scale, especially when high precision and tight tolerances are dominant factors.

To date, investigations of size effects on totality and formability in microforming applications are generally limited to tensile tests of thin sheets and few micro deep drawing and micro bulge forming studies. Formability during tensile tests has been simply characterized by elongation until failure. For the biaxial experiments, limiting drawing ratio and maximum bulge height have been used to characterize the formability during micro deep drawing and micro bulge forming respectively. This limited formability analysis is not sufficient to understand the size effect, which are known as the effects of miniaturization on microforming processes, on deformation and formability at the microscale. More detailed analysis of strain distributions and limiting strains during microforming of thin sheets is needed to be able to predict deformability limits for thin sheets and minimize trial and error runs that are conventionally performed to master the know-how of a micro-metal forming process. The consequences of such prediction are better optimization of process parameters and a reduced overall manufacturing cost.

In order to conduct the specified analysis, testing apparatus and equipment that will accommodate microscale testing is needed. Microscale testing by conventional testing equipment cannot demonstrate the degree of precision nor account for the effect which is considered minor at the macroscale level: such as friction which has proven to increase drastically as process miniaturization is increased. Forming limit diagrams (FLDs) are an effective tool for studying the formability of sheet metals at different strain conditions. The present invention relates to an integrated approach for investigating size effects and the formability of thin sheets for microforming applications.

SUMMARY OF THE INVENTION

In accordance with the purposes of the present invention as described herein, a method is provided for predicting sheet formability at a microscale level. That method may be broadly defined as including the steps of providing a grid pattern on a test sheet, bulging that test sheet to a hemispherical shape until a crack is initiated on the surface of the test sheet, detecting the initiation of the crack, acquiring two images of the surface adjacent to the crack and calculating surface strain on the test sheet.

More specifically describing the method, the providing step may include a photolithography process for forming the grid pattern in a predetermined shape. That predetermined shape might be a circle or a square.

The lithography process includes applying a photoresist compound to the surface of the test sheet, baking the test sheet to form a thin layer of photoresist compound on the surface, applying a photomask overlying the thin layer of photoresist compound, beaming UV rays through the photoresist mask onto the thin layer of photoresist compound and removing any portion of the thin layer of photoresist compound exposed to the UV rays. The removal of the photoresist compound may be completed by dissolving any portion of the layer of photoresist compound exposed to UV rays so that the remaining portion of the layer of photoresist compound defines the grid pattern. A chemical developer may be used in the dissolving step. That chemical dissolver may be selected from a group of materials consisting of potassium borates, tetramethylammonium hydroxide, water, and mixtures thereof.

In an alternative embodiment of the present invention, the photolithography process may include applying a negative photoresist compound to the surface of the test sheet, baking the test sheet to form a thin layer of photoresist compound on the surface, applying a photoresist mask overlying a thin layer of photoresist compound, beaming UV rays through the photoresist mask onto the thin layer of photoresist compound and removing any portion of the thin layer of photoresist compound exposed to the UV rays. This alternative method also includes the dissolving of any portion of the layer of photoresist compound exposed to the UV rays so that the remaining portion of the layer of photoresist compound defines an inverted image of the grid pattern.

In accordance with additional aspects of the present invention, the method may further include the immersing of the test sheet with a layer of negative photoresist compound into a chemical etchant, which varies with the material of the tested sheet, so that any portion of the test sheet with no negative photoresist compound is etched to a certain depth and accordingly the grid pattern is then identified.

The method may be further described as including the using of a punch-die microforming machine to bulge the test sheet. Further, the detecting of the initiation of the crack may include the measuring of a pre-determined drop in force required to provide bulging of the test sheet. In addition, the acquiring of two images of the surface adjacent the crack may include scanning the test sheet with a scanning electron microscope.

In the following description there is shown and described several different preferred embodiments of this invention, simply by way of illustration of some of the modes best suited to carry out the invention. As it will be realized, the invention is capable of other different embodiments and its several details are capable of modification in various aspects all without departing from the invention. Accordingly, the drawings and descriptions will be regarded as illustrative in nature and not as restrictive.

BRIEF DESCRIPTION OF THE DRAWINGS

The accompanying drawings incorporated herein and forming a part of the specification, illustrate several aspects of the present invention, and together with the description serve to explain certain principles of the invention. In the drawings.

Reference will now be made in detail to the present preferred embodiments of the invention, examples of which are illustrated in the accompanied drawing.

DETAILED DESCRIPTION OF THE OF THE INVENTION

Figure 1:
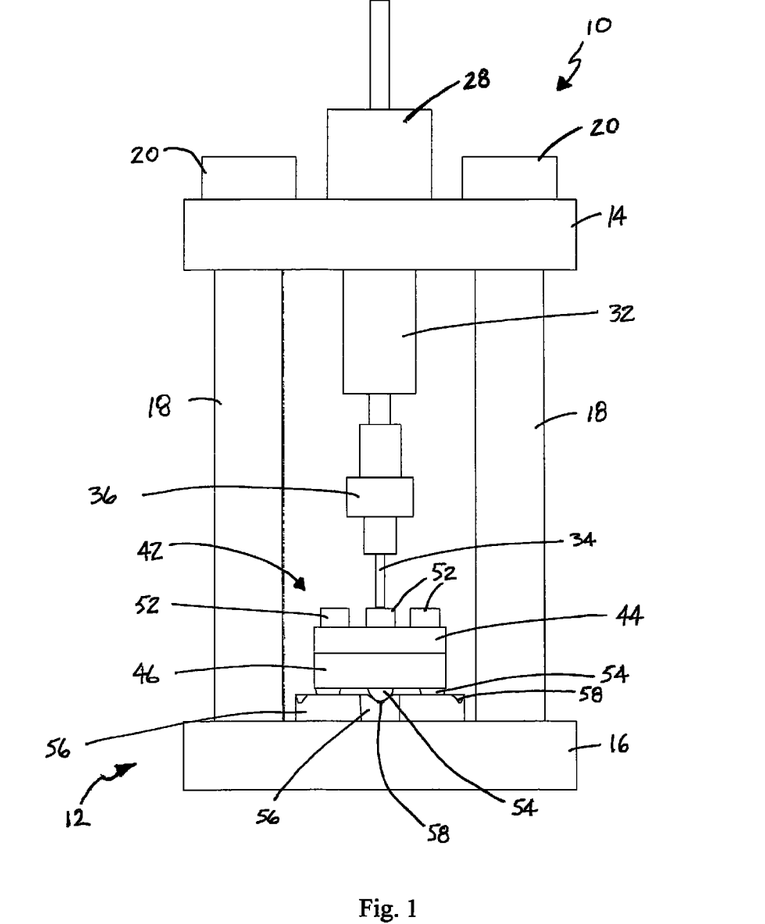
FIG. 1 is a schematical perspective view of the test apparatus of the present invention.
Figure 2:
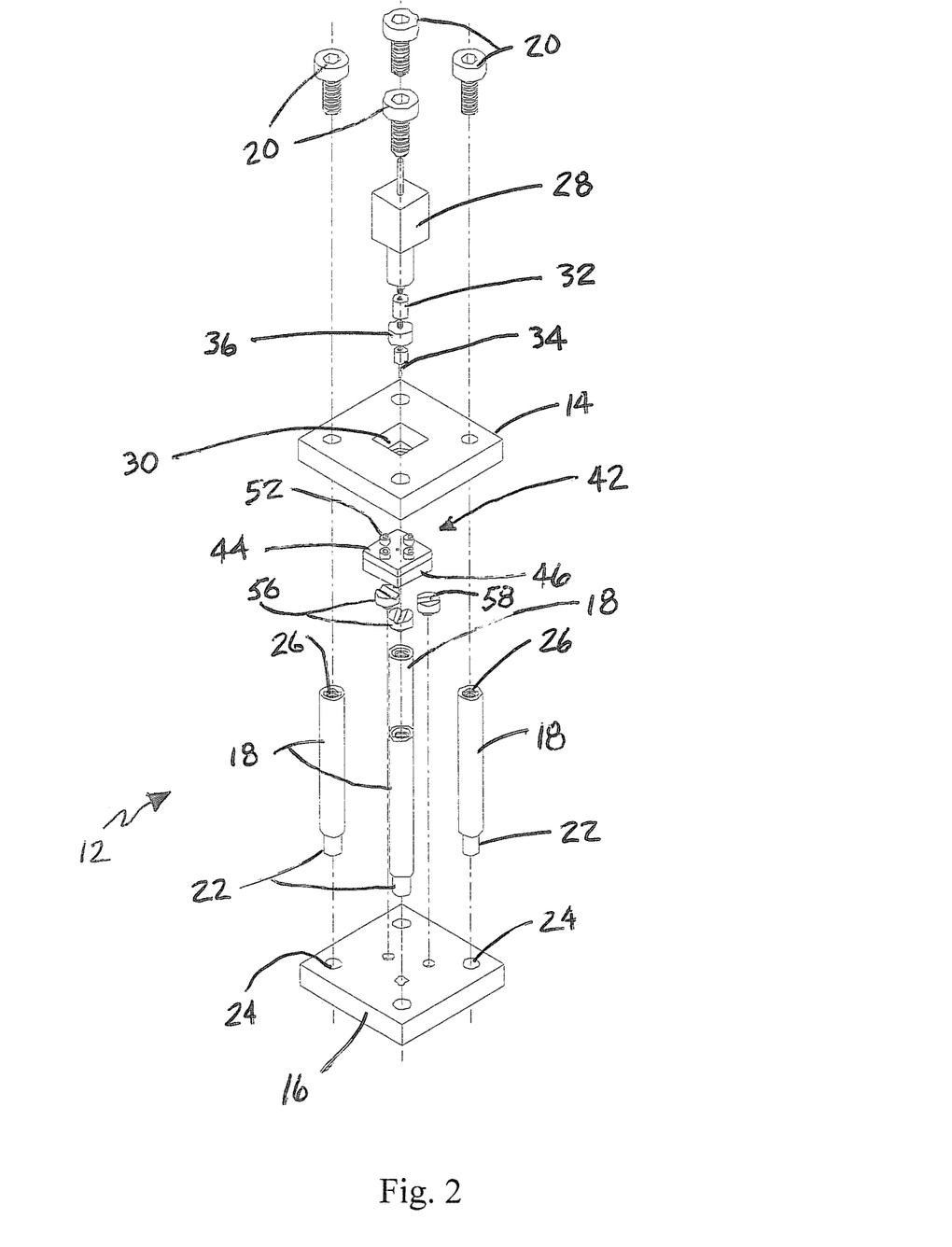
FIG. 2 is a schematical, exploded perspective view of the test apparatus illustrated in FIG. 1.

Reference is now made to FIGS. 1 and 2 showing the test apparatus of the present invention for the punch die microforming of a test specimen or thin sheet of metal material. As illustrated, the apparatus 10 includes a frame 12 comprising a top plate 14, a bottom plate 16, a series of four support columns 18 and four fastening bolts 20. Each of the columns 18 includes a threaded end 22 received in a cooperating threaded aperture 24 provided in the base plate 16. Each of the four columns 18 are tightened to the base plate 16. The top plate 14 is then positioned on the upper end of the columns 18 and the fastening bolts 22 are then secured in threaded bores 26 in the ends of the columns in order to secure the frame 12 together. A linear actuator 28 is secured in a central opening 30 provided in the top plate 14 by any appropriate means. Linear actuator 28 includes a coupling nut 32 that holds a punch 34. A load cell 36 is provided to allow one to monitor the load placed on a test specimen 40 during testing as described in greater detail below.

Figure 3:
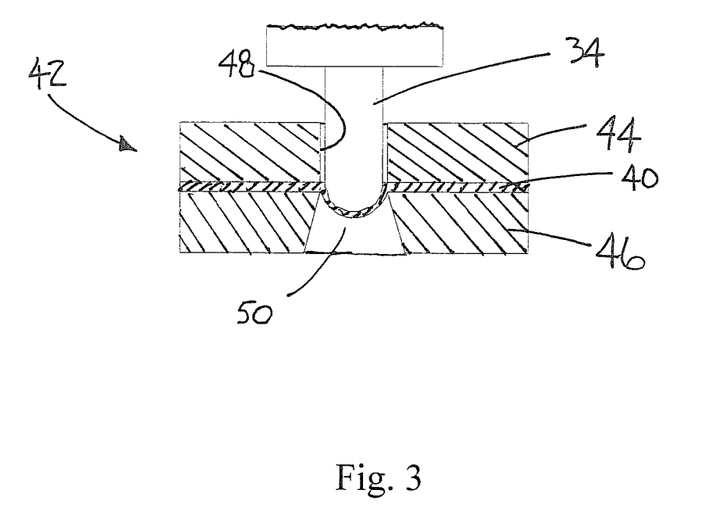
FIG. 3 is a partial schematical and cross-sectional view showing the punch bulging of a test specimen or thin sheet held between the two sections of the die.

The test specimen 40 is held in a die, generally designated by reference numeral 42. The die 42 comprises a first or upper section 44 and a second or lower section 46. As best illustrated in FIG. 3, the test specimen 40 is held between the two sections 44, 46 of the die 42. As illustrated, the first or upper section 44 includes a cylindrical opening 48 while the second or lower section 46 includes a tapered opening 50. The test specimen 40 is initially a flat or planar sheet of metal having a thickness of between about 10 μm and about 150 μm. In one possible embodiment, the test specimen is a square with each edge having a length of between about 1 mm and about 9 mm. The test specimen 40 is positioned on the second or lower section 46 of the die 42. The first or upper section 44 of the die 42 is then positioned over the test specimen 40 so that the test specimen is sandwiched between the upper and lower sections 44, 46. The die 42 is then closed by tightening a series of locking nuts or screws 52 to securely hold the test specimen 40 in position. The die 42 and test specimen 40 are then positioned in the apparatus 10.

A series of three hemispheres 54 are secured to the lower face of the second or lower section 46 of the die 42. The hemispheres 54 may be made from aluminum, steel, sintered carbide or other appropriate material. The hemispheres 54 may be attached to the bottom wall of the second or lower die section 46 by epoxy or other appropriate means.

As illustrated in drawing FIGS. 1 and 2, the die 42 and the test specimen 40 held therein are positioned on the bottom plate 16 on a series of three kinematic supports 56. Each kinematic support 56 includes a v-shaped groove 58. The kinematic supports 56 are made of a hard metal material such as steel or sintered carbide so as to avoid any possible distortion of the v-shaped grooves 58 during testing. The kinematic supports 56 are anchored to the base plate 16 by press fitting in appropriately sized apertures (not shown) or by other appropriate means.

When the die 42 is properly positioned in the apparatus 10, the hemispheres 54 carried on the second or lower die section 46 are each received in one of the v-shaped grooves 58 of the kinematic supports. In addition, the cylindrical opening 48 and the first or upper die section 44 is aligned with the punch 34 carried by the linear actuator 28 (see also FIG. 3).

Figure 5:
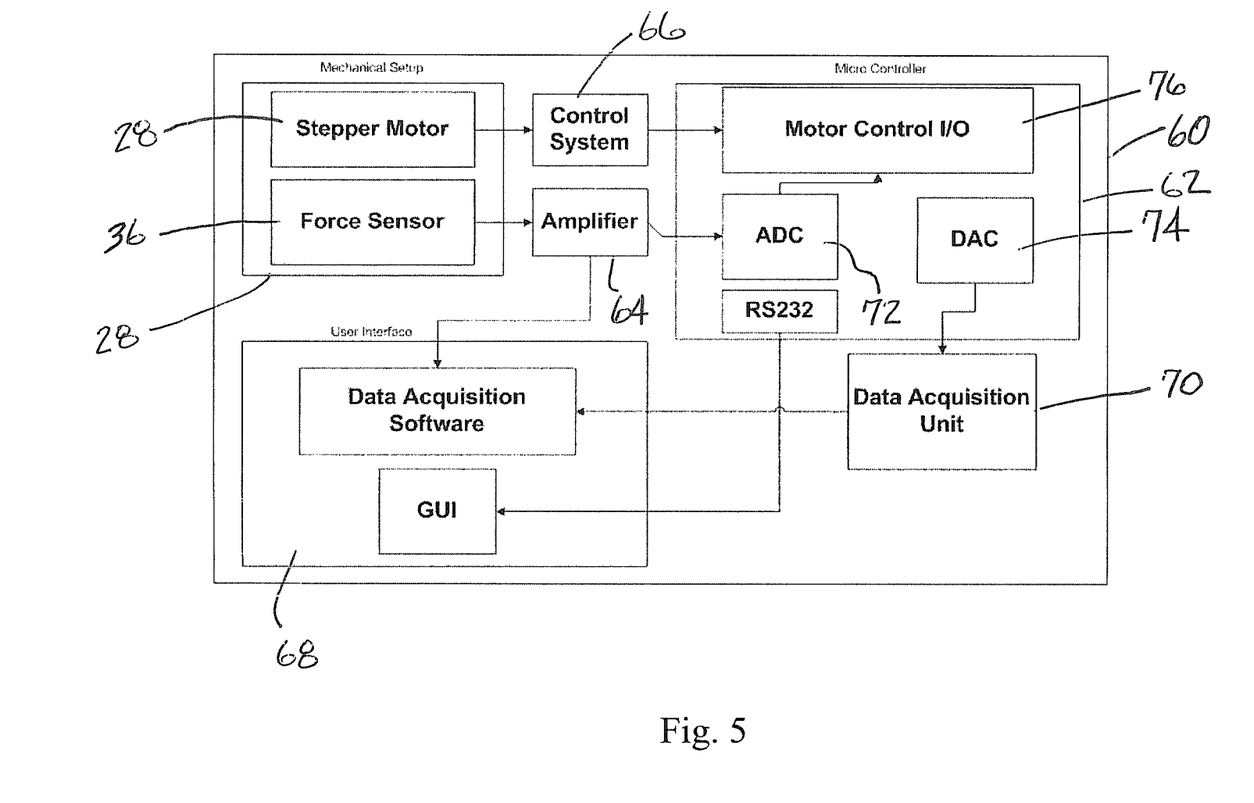
FIG. 5 is a schematical block diagram of the control circuit of the present invention.

The apparatus also includes a control circuit illustrated in FIG. 5 and generally designated by reference numeral 60. The control circuit 60 consists of a microcontroller 62, an amplifier 64 for the load cell 36, a control system 66 for the linear actuator 28, a user interface 68 (comprised of the GUI Graphical User Interface), and a DAQ (Data Acquisition) Software which allows the user to view the raw data. More specifically, the electrical system is comprised of the electric control system 66 provided with the linear actuator 28, the amplifier 64 for signals from the load cell 36, the microcontroller 62, and a data acquisition unit 70. The input signals from the linear actuator 28 (and more specifically, the stepper motor of the linear actuator) are fed into the control system 66. The linear actuator 28 is interfaced with the microcontroller 62 to more efficiently control the actuator 28.

The load cell 36 reads voltage depending on the amount of force being pressed against it, the higher the force, the higher the voltage. The load cell's or force sensor's voltage is then routed through the amplifier 64, and into the analog digital converter (ADC) 72 in the microcontroller 62. To reduce the noise in the lines between the amplifier 64 and the ADC 72, an appropriate filter capacitor (not shown) was placed.

The microcontroller 62 used for this specific control setting may be, for example, the Silicon Labs 8051×120. The processor of this microcontroller 62 includes a 12-bit analog to digital converter, a 12-bit digital to analog converter, two analog comparators, a UART serial port, and 8448 bytes internal data RAM. For this specific application, only the analog digital converter 74 uses the digital value of the number of steps taken by the motor (displacement) of the linear actuator 28 and converts it to an analog signal that is used as an input in the data acquisition unit 70 to display position. The acquisition unit 70 used for this application may be, for example, the National Instruments NI-6009 USB DAQ. The DAQ 70 has an input resolution of 14-bit, with a range of +1 to ±20 Volts. The DAQ's operation involves reading in the force as a voltage from the amplifier 64, and displacement as a voltage from the control system 66.

There are several functional components that comprise the firmware implementation (instructions that are stored permanently in read-only memory). The first is the linear actuator control system. Moving the motor up and down is a simple task due to the use of an off the shelf control system that was provided by the manufacturer. Outputs from the GPIO of the microcontroller 62 simply feed the motor control 76 a few analog signals which represent resolution (half step or full step), direction, and the motor start/stop control. The more complicated control logic is located in the specific features that determine how the motor operates.

The user can select four different parameters to describe the motor operation during the experiment: special force safety measures, speed, displacement, maximum force sensitivity, and dwell time.

The simplest design is the speed displacement software functions. It is only a matter of calculating some depth conversions, and then deriving the speed using basic laws of mechanics. Dwell time is implemented by simply making the machine pause after the punch is executed for a user defined amount of time in milliseconds.

A safety feature was designed such that at a certain maximum value (a force value that could damage the mechanical equipment); the machine would be forced to halt, and raise the punch upwards all the way. The feature was implemented by using a software interrupt located inside the 8051 ADC architecture. The ADC 72 has two comparators, in which certain threshold values can be specified for the ADC. Once the ADC 72 reading goes above the values written in the comparator's registers, if the interrupts are enabled, it will display a flag, and interrupt the machine. The feature simply loads the register with a value that the programmer assumes dangerous, and when the ADC 72 reaches a value larger than the programmer specified one, the system will halt, preventing any damage to delicate instruments.

Figure 6:
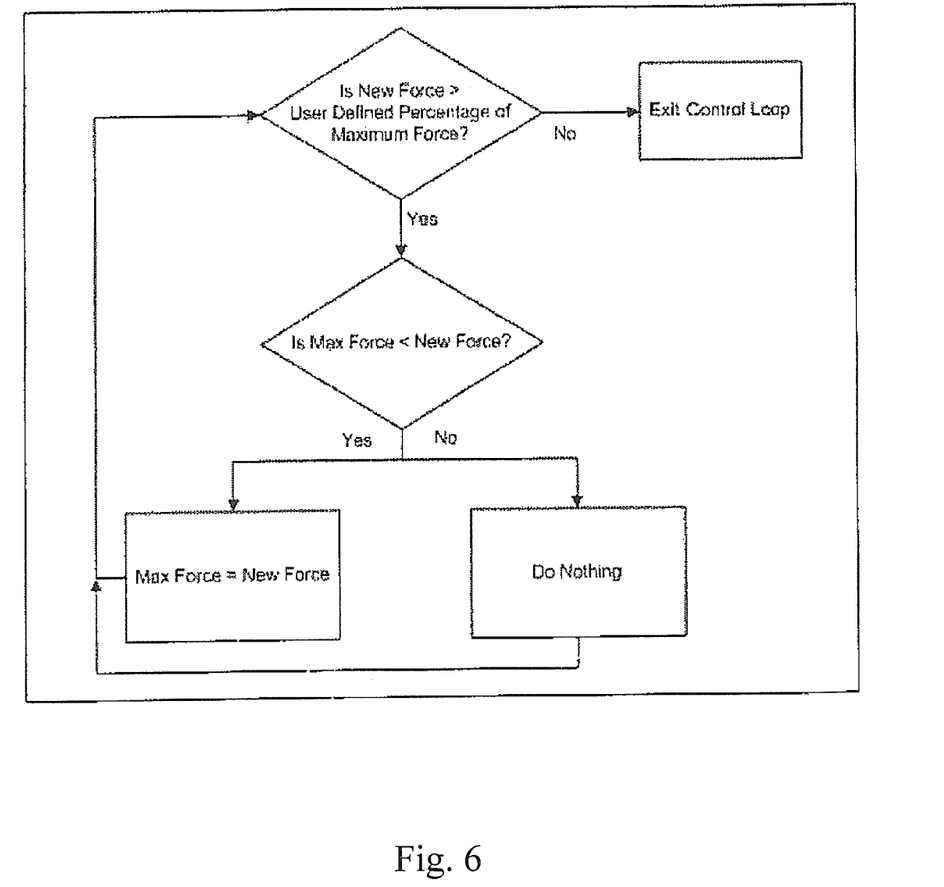
FIG. 6 is a schematic block diagram illustrating the logic used to prevent the punch from penetrating through the test specimen during testing.

The final design specification for the firmware section was the maximum force sensitivity setting. This setting allows the user to specify a percentage drop from the maximum force at which the test would be over, in order to prevent the punch from penetrating through the specimen. The logic behind the implementation is shown in FIG. 6.

Every time a step is taken by the stepper motor of the linear activator 28, a "new force" voltage reading is saved into a variable, and compared with another variable called "max force." If the new force is larger than the max force then the slope of the force is still rising, and new force is stored into the max force variable. If the slope begins to fall, the new force should fall below the maximum force, and maximum force is not altered. Once the new force is below the maximum force, multiplied by the user defined percentage, the machine should halt the experiment, and return to home position.

Figure 7:
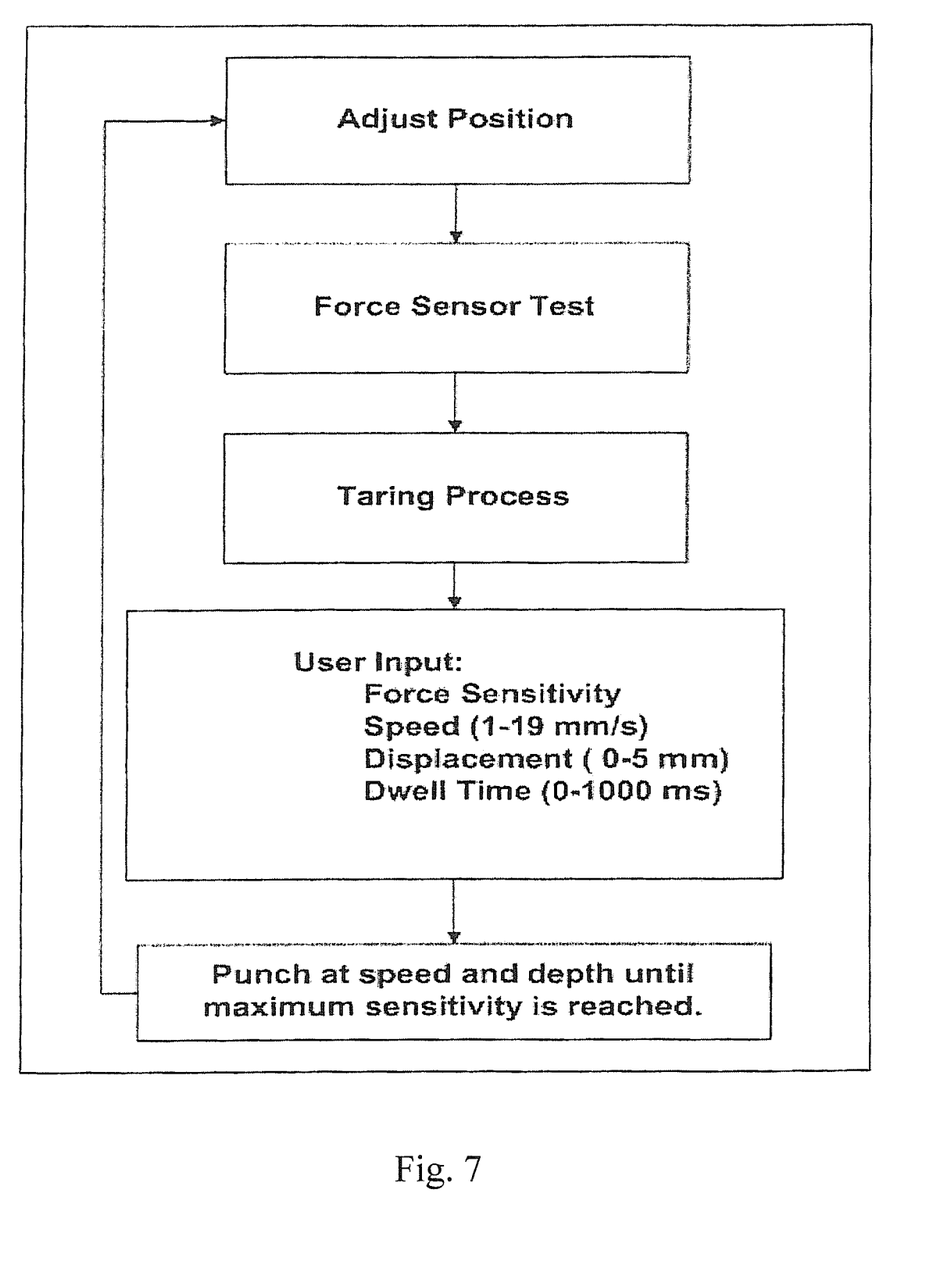
FIG. 7 is a schematic block diagram illustrating the flow of information on the user's input screen.

The user interfaces with the machine by selecting (as stated earlier) speed, maximum force sensitivity, displacement (depth), and dwell time. During the experiment the main points of interest are how the metal reacts to a certain force, at a certain force, at a certain depth, and at a certain speed. Once the user selects these parameters, the rest of the experiment is fully automated. The flow of the user's input screen is shown in FIG. 7.

Figure 4A:
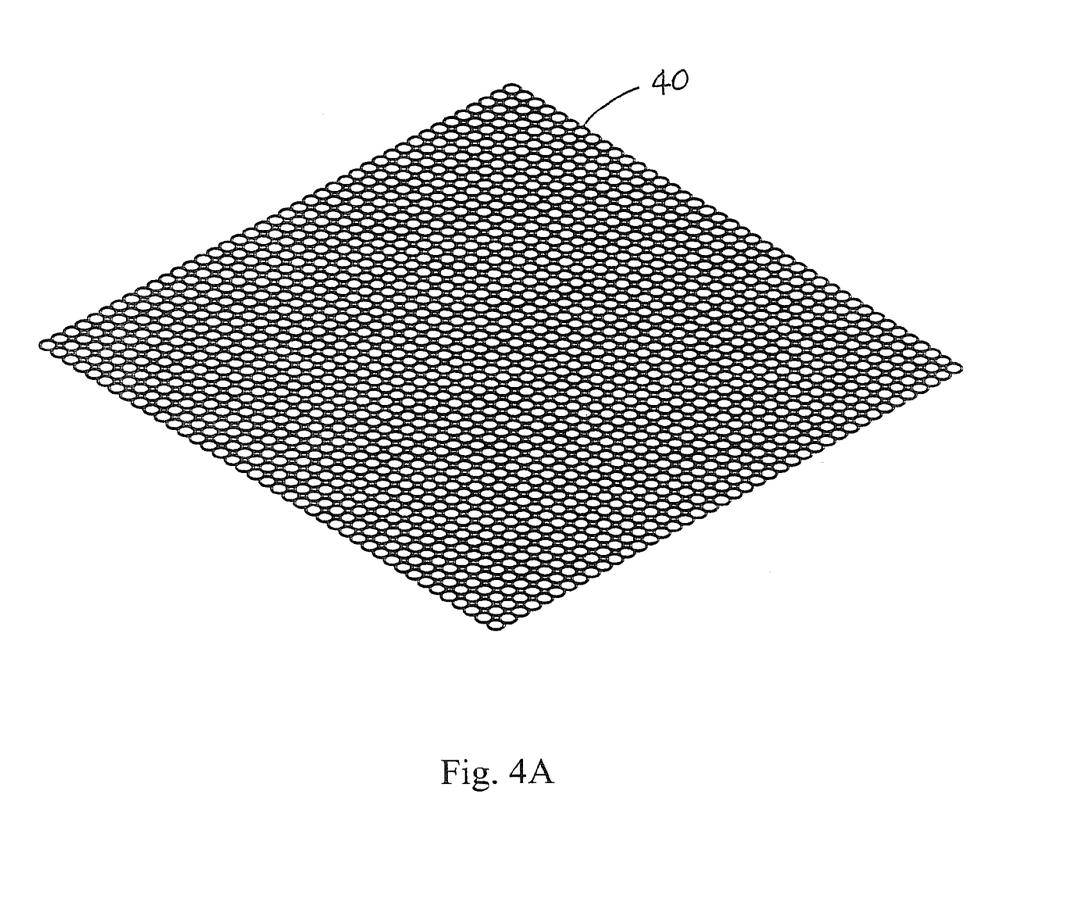
FIGS. 4A and 4B are respective perspective views of the original planar test specimen and the bulged or deformed test specimen showing a crack following testing.
Figure 4B:
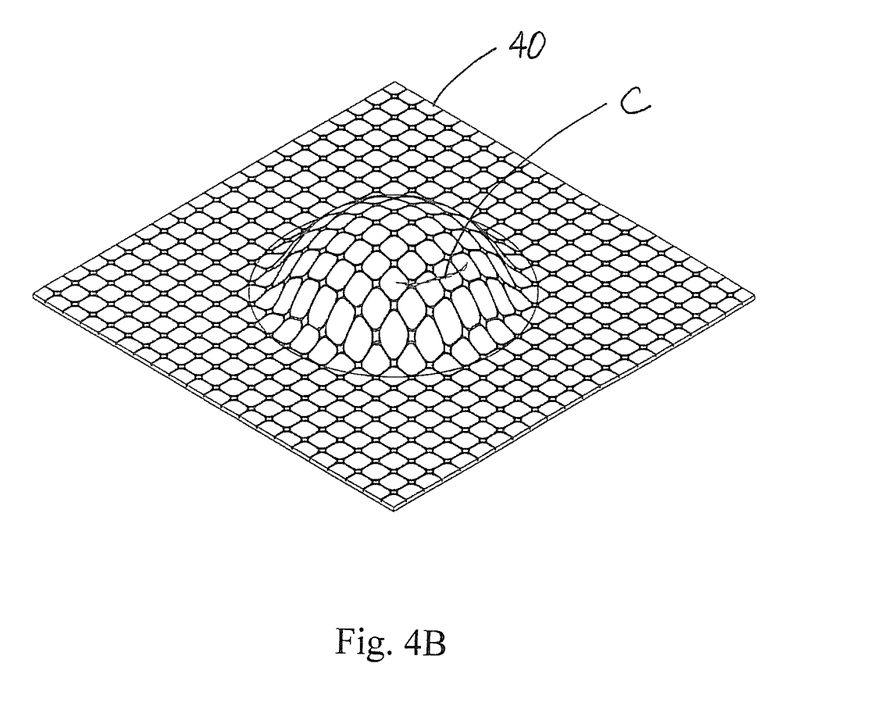

The method of predicting sheet formability at a microscale level utilizing the apparatus 10 will now be discussed in detail. Initially, it is necessary to provide a grid pattern on the thin sheet or test specimen 40. Such a grid pattern is illustrated in FIGS. 4A and 4B. Typically the grid pattern is formed as a series of predetermined shapes including, for example, circles and/or squares. In one possible embodiment, a photolithography process is used to form the grid pattern. One possible photolithography process for this purpose includes the steps of applying a photoresist compound to the surface of the test sheet 40, baking the test sheet to form a thin layer of photoresist compound on that surface, applying a photoresist mask overlying the thin layer of photoresist compound, beaming UV rays through the photoresist mask onto the thin layer of photoresist compound and removing any portion of the thin layer of photoresist compound exposed to the UV rays. The removal of the exposed photoresist compound may be accomplished by dissolving with a chemical developer. Such a chemical developer may, for example, be selected from a group of commercial compounds consisting of potassium borates, tetramethylammonium hydroxide, water, and mixtures thereof.

An alternative photolithography process useful in the present invention includes the steps of applying a negative photoresist compound to the surface of the test sheet 40, baking the test sheet to form a thin layer of photoresist compound on the surface, applying a photoresist mask overlying a thin layer of photoresist compound, beaming UV rays through the photoresist mask onto the thin layer of photoresist compound and removing any portion of the thin layer of photoresist compound exposed to the UV rays. In this embodiment the removing step may also include dissolving any portion of the layer of photoresist compound exposed to the UV rays so that the remaining portion or layer of photoresist compound defines an inverted image of the grid pattern. Once again the chemical developer described above may be used in the dissolving process. Typically the test sheet 40 is immersed in to the chemical developer in order to complete the dissolving step. In this method, a grid pattern may then be printed onto the specimen 40 by dipping the specimen into a chemical etchant which may consist of phosphoric acid, nitric acid, acetic acid, and other chemical mixed with water depending on the material used.

Once a test specimen 40 has been provided within an appropriate grid pattern, the test specimen is loaded into the die 42 in the manner described above. The surface of the test specimen 40 including the grid pattern is loaded downward, facing toward the second or lower section 46 of the die 42. The punch die microforming apparatus 10 is then used to bulge the test sheet 40 to a hemispherical shape (see FIG. 4B) until a crack C is initiated on the surface of the test sheet. The method further includes detecting the initiation of this crack C by measuring a predetermined drop in force required to provide the bulging of the test sheet 40. At least two images are then acquired of the surface of the test sheet 40 adjacent to crack C. This may be accomplished by scanning the test sheet with a scanning-electron microscope. Data from the acquired images is then used to calculate the surface strains on the test sheet 40. This may be accomplished using the commercial software ASAME (Automated Strain Analysis and Measurement Environment). In order for this software to measure strains accurately, a target element having a square grid on each side which enables the software to recognize distances in three-dimensional space has to be used. For surface strain measurements in microbulge thin sheets, the target element may be fabricated with a 0.5 mm side resulting from a scaling of 50 folds from the original target, which has 25 mm side length.

The following example is presented to further illustrate the invention, and is not to be considered as limited thereto.

Photolithography:

The photolithography technique was applied for marking a grid pattern on the surface of thin sheets, similar to the technique of marking at the macroscale obtained by electro-chemical etching. A micro-laser-etched photomask was developed for this purpose. The photomask consists of a rectangular grid of circles with each circle having a diameter of 50 μm. The applied photoresist was an AZ5214 photoresist supplied by DATAK Corporation. This photoresist was spin coated on the thin sheets at 4000 rpm for 30 seconds to form a 1.5 μm uniform film. Coated specimens were then baked at 110° C. for one minute to ensure proper bonding between the photoresist thin sheets. By exposing coated specimens to ultra-violet rays through the photomask and then baking them at 110° C. for one minute, the exposed part of the photoresist nucleated. The final stage was developing, where exposed coated specimens were immersed into an AZ400 positive developer by DATAK Corporation for one minute. The remainder was a well bonded and defined pattern of circles. This marking technique resembles the spray painting technique for capturing in-situ deformation using the ARAMIS optical deformation and strain measurement system where a random pattern with good contrast has to be applied on the surface for characterizing formability.

Microforming:

The microforming apparatus used in this experimental procedure is illustrated in FIGS. 1 and 2. The hemispherical punch tip was 1 mm and 1.5 mm in diameter. The punch was mechanically driven by a stepper-motor-driven linear actuator which demonstrated a high precision factor of 1.5 μm and 3 μm per step. Although the die hole was just slightly larger than 1.5 mm (the punch diameter), the require specimen size was 9×9 mm for facilitating handling of samples and applying proper gripping with the directions.

For holding thin sheet specimens, the die was fabricated and clamping of sheets was applied by a single screw mechanism. In order to ensure proper alignment between the punch and the die hole, a kinematic coupling mechanism with a six-point contact layout was fixed between the bottom of the die and the fixture frame. The die arrangement ensured enough clamping forces to restrict thin sheets from drawing into the die opening while forming. An electronic processor was developed for controlling speeds and depths of the forming punch. A data acquisition system complemented the setup to measure holding profiles along with the forming process. Thin sheets were deformed into a hemisphere until the initiation of a crack on the surface which was detected by achieving a certain drop in force recorded by the embedded processor.

Failure Capture by SEM Imaging:

Scanning electronic microscopy was used to assist in capturing the failure area on the tested thin sheets. Images of the deformed specimen at the vicinity of the formed crack were captured using a HITACHI 3200 SEM machine. By identifying random cracking of the deformed circle markings on top of the bulged sheet, a solid justification was drawn for providing the straining of the marking layer along with the bulged sheet.

Analysis of Deformed Thin Sheets:

Preliminary analysis of the deformed grids was conducted by manual calculation of the deformed circles around the formed crack from SEM images, assuming the surface around cracks were flat.

Figure 8:
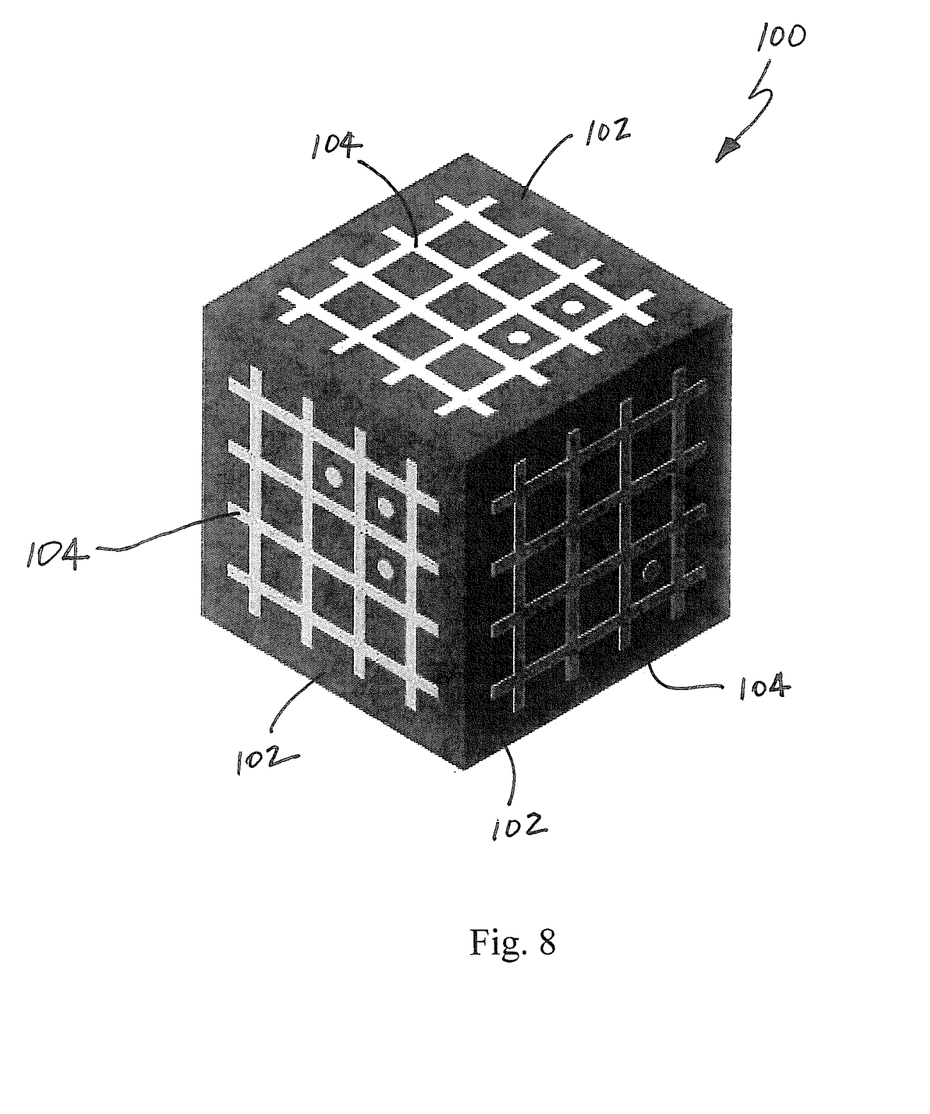
FIG. 8 is a perspective view of a target element used in collecting data to allow for strain analyses.

To accommodate for three-dimensional measurement in calculating surface strains of the deformed grids, which is an essential requirement for assuring proper and correct results, the ASAME (Automated Strain Analysis and Measurement Environment) was used. In order for the software to measure strains accurately, a target element, which enables the software to recognize accurate dimensions in three-dimensional space, was required. The target element, generally designated by reference number 100 in FIG. 8, demonstrates a size of 25 mm on each side 102 and contained an identified grid 104. Since the deformed grids could not be captured by a conventional digital camera, and SEM imaging was used to identify the deformed grids around the crack area instead, a cubic target which could be viewed around the vicinity of the micro crack was needed. For this purpose, a target element that holds a scaled layout of the actual commercial target was micromachined with a 500 μm side resulting from scaling down the dimensions of the original target element by 50 folds. This microtarget element was scaled down accordingly with the scaling of the circular grid pattern such that the transferred images would hold the same proportion to the actual dimensions in the macroscale. Only three faces of the micro-target were micromachined on a corner of ¼" cube since the software identifies only three faces, and for handling issues.

The foregoing description of the preferred embodiments of the present invention have been presented for purposes of illustration and description. It is not intended to be exhaustive or to limit the invention to the precise form disclosed. Obvious modifications or variations are possible in light of the above teachings. The embodiments were chosen and described to provide the best illustration of the principles of the invention and its practical application to thereby enable one of ordinary skill in the art to utilize the invention in various embodiments and with various modifications as are suited to the particular use contemplated. All such modifications and variations are within the scope of the invention as determined by the appended claims when interpreted in accordance with the breadth to which they are fairly, legally and equitably entitled. The drawings and preferred embodiments do not and are not intended to limit the ordinary meaning of the claims in their fair and broad interpretation in any way.

What is claimed:

1. A method of predicting sheet formability at a microscale level, comprising:
   printing a grid pattern on a surface of a test sheet;
   bulging said test sheet to a hemispherical shape until a crack is initiated on said surface of said test sheet and said grid pattern printed on said surface of said test sheet is deformed;
   detecting the initiation of said crack;
   acquiring two images of said deformed grid pattern on said surface adjacent said crack; and
   calculating surface strains on said test sheet from said deformed grid pattern.

2. The method of claim 1, wherein said printing step includes using a photolithography process and forming said grid pattern in a predetermined shape.

3. The method of claim 2, including using a circle as said predetermined shape.

4. The method of claim 2, including using a square as said predetermined shape.

5. The method of claim 2, wherein said photolithography process includes: (a) applying a photoresist compound to said surface of said test sheet; (b) baking said test sheet to form a thin layer of photoresist compound on said surface; (c) applying a photoresist mask overlying said thin layer of photoresist compound; (d) beaming UV rays through said photoresist mask onto said thin layer of photoresist compound; and (e) removing any portion of said thin layer of photoresist compound exposed to said UV rays.

6. The method of claim 5, wherein said removing step includes dissolving any portion of said layer of photoresist compound exposed to said UV rays so that a remaining portion of said layer of photoresist compound defines said grid pattern.

7. The method of claim 6 including using a chemical developer in said dissolving step.

8. The method of claim 7 including selecting said chemical developer from a group of materials consisting of potassium borates, tetramethylammonium hydroxide, water, and mixtures thereof.

9. The method of claim 2, wherein said photolithography process includes: (a) applying a negative photoresist compound to said surface of said test sheet; (b) baking said test sheet to form a thin layer of photoresist compound on said surface; (c) applying a photoresist mask overlying said thin layer of photoresist compound; (d) beaming UV rays through said photoresist mask onto said thin layer of photoresist compound; and (e) removing any portion of said thin layer of photoresist compound exposed to said UV rays.

10. The method of claim 9, wherein said removing step includes dissolving any portion of said layer of photoresist compound exposed to said UV rays so that a remaining portion of said layer of photoresist compound defines said grid pattern.

11. The method of claim 10 including using a chemical developer in said dissolving step.

12. The method of claim 11, including selecting said chemical developer from a group of materials consisting of potassium borates, tetramethylammonium hydroxide, water, and mixtures thereof.

13. The method of claim 10 further including immersing said test sheet with said layer of negative photoresist compound in chemical etchant so that any portion of said test sheet with no negative photoresist compound defines said grid pattern.

14. The method of claim 13, wherein said removing step includes dissolving any portion of said layer of negative photoresist compound exposed to said UV rays so that a remaining portion defines said grid pattern.

15. The method of claim 1, including using a punch-die microforming apparatus to bulge said test sheet.

16. The method of claim 1, wherein detecting the initiation of said crack includes measuring a predetermined drop in force required to provide bulging of said test sheet.

17. The method of claim 1, wherein acquiring two images of said surface adjacent said crack includes scanning said test sheet with a scanning-electron microscope.

18. A punch-die microforming apparatus, comprising:
a frame;
a test specimen having a surface printed with a grid pattern;
a die for holding said test specimen on said frame;
a linear actuator carried by said frame;
a punch carried by said linear actuator;
a plurality of kinematic supports carried on said frame;
a plurality of hemispheres provided on said die, said plurality of hemispheres supporting said die on said plurality of kinematic supports.

19. The apparatus of claim 18 wherein said die includes a first section and a second section and said test specimen is held between said first section and said second section of said die.

20. The apparatus of claim 19 wherein said punch passes through an opening in said first section of said die to engage said test specimen and said plurality of hemispheres are provided on said second section of said die.

* * * * *